(12) United States Patent
Simon et al.

(10) Patent No.: US 6,272,384 B1
(45) Date of Patent: Aug. 7, 2001

(54) MICROWAVE THERAPY APPARATUS

(75) Inventors: Eric Simon; Olivier Lassal, both of Vaulx En Velin (FR)

(73) Assignee: Urologix, Inc., Minneapolis, MN (US)

( * ) Notice: Subject to any disclaimer, the term of this patent is extended or adjusted under 35 U.S.C. 154(b) by 0 days.

(21) Appl. No.: 09/411,475

(22) Filed: Oct. 1, 1999

(30) Foreign Application Priority Data

May 27, 1999 (EP) .................................................. 99401264

(51) Int. Cl.$^7$ ........................................................ A61F 2/00
(52) U.S. Cl. .............................. 607/101; 607/102; 607/96
(58) Field of Search ............................... 607/96, 101–105, 607/113, 116, 154, 156

(56) References Cited

U.S. PATENT DOCUMENTS

| | | |
|---|---|---|
| 4,190,053 | 2/1980 | Sterzer . |
| 4,375,220 | 3/1983 | Matvias . |
| 4,601,296 | 7/1986 | Yerushalmi . |
| 4,662,383 | 5/1987 | Sogawa et al. . |
| 4,676,258 | 6/1987 | Inokuchi et al. . |
| 4,813,429 | 3/1989 | Eshel et al. . |
| 4,967,765 | 11/1990 | Turner et al. . |
| 5,007,437 | 4/1991 | Sterzer . |
| 5,234,004 | 8/1993 | Hascoet et al. . |
| 5,304,214 | 4/1994 | DeFord et al. . |
| 5,330,518 | 7/1994 | Neilson et al. . |
| 5,344,435 | 9/1994 | Turner et al. . |
| 5,391,197 | 2/1995 | Burdette et al. . |
| 5,404,881 | 4/1995 | Cathaud et al. . |
| 5,413,588 | 5/1995 | Rudie et al. . |
| 5,423,811 | 6/1995 | Imran et al. . |
| 5,433,740 | 7/1995 | Yamaguchi . |
| 5,464,437 | 11/1995 | Reid et al. . |
| 5,464,445 | 11/1995 | Rudie et al. . |
| 5,480,417 | 1/1996 | Hascoet et al. . |
| 5,496,271 | 3/1996 | Burton et al. . |
| 5,509,929 | * 4/1996 | Hascoet et al. .................. 604/101 |
| 5,520,684 | 5/1996 | Imran . |
| 5,545,137 | 8/1996 | Rudie et al. . |
| 5,575,811 | 11/1996 | Reid et al. . |
| 5,620,480 | * 4/1997 | Rudie .................................. 607/101 |

(List continued on next page.)

FOREIGN PATENT DOCUMENTS

| | | |
|---|---|---|
| 9940126 | 5/1999 | (EP) . |
| WO 94/02204 | 2/1994 | (WO) . |
| WO 94/26188 | 11/1994 | (WO) . |
| WO 94/28809 | 12/1994 | (WO) . |

OTHER PUBLICATIONS

M. Devonec et al., "Transurethral Microwave Thermotherapy (TUMT) in Patients with Benig Prostatic Hypertrophy," Urology Departments, Antiquaille Hospital, Lyon, France.

M. Devonec et al., "Transurethral Microwave Thermotherapy (TUMT)" *1992 Monographs in Urology*, vol. 13, No. 4.

P.S. Debicki et al., "Cooled Microwave Transrectal Applicator with Adjustable Directional Beam for Prostate Treatment", *international Journal of Hyperthermia*, vol. 11, No. 1, Jan.–Feb. 1995.

Michael L. Bute, MD., "Transurethral Thermotherapy For Benig Prostatic Hypertrophy" *Mediguide to Urology*, vol. 4, Issue 6.

*Primary Examiner*—Roy Gibson
(74) *Attorney, Agent, or Firm*—Kinney & Lange, P.A.

(57) ABSTRACT

The invention relates to an apparatus for treating the prostate. The apparatus includes a urethral probe, a microwave generator, and coolant circulating system. The urethral probe has microwave antenna and ducts for circulating a coolant. The microwave generator applies microwave energy to the microwave antenna. The coolant circulating system circulates the coolant and controls the temperature of the coolant.

20 Claims, 2 Drawing Sheets

U.S. PATENT DOCUMENTS

| | | |
|---|---|---|
| 5,628,770 | 5/1997 | Thome et al. . |
| 5,642,382 | 6/1997 | Juan . |
| 5,643,335 | 7/1997 | Reid et al. . |
| 5,676,692 | 10/1997 | Sanghvi et al. . |
| 5,733,319 | 3/1998 | Neilson et al. . |
| 5,755,754 | 5/1998 | Rudie et al. . |
| 5,792,070 | 8/1998 | Kauphusman et al. . |
| 5,800,486 | 9/1998 | Thome et al. . |
| 5,843,144 | 12/1998 | Rudie et al. . |
| 5,861,021 | 1/1999 | Thome et al. . |
| 5,899,932 | 5/1999 | Dann et al. . |
| 5,916,240 | 6/1999 | Rudie et al. . |
| 5,916,241 | 6/1999 | Rudie et al. . |
| 5,931,860 | 8/1999 | Reid et al. . |
| 5,938,692 | 8/1999 | Rudie . |
| 5,987,360 | 11/1999 | McGrath et al. . |
| 5,992,419 | 11/1999 | Sterzer et al. . |
| 6,007,571 * | 12/1999 | Neilson et al. ............... 607/105 |
| 6,009,351 * | 12/1999 | Flachman ...................... 607/101 |
| 6,122,551 * | 9/2000 | Rudie et al. .................. 607/102 |

\* cited by examiner

MICROWAVE THERAPY APPARATUS

FIELD OF THE INVENTION

The invention relates to the field of microwave therapy, and more specifically to the control of microwave power in a microwave therapy apparatus.

BACKGROUND OF THE INVENTION

EP-A-370 890 in the name of Technomed Medical Systems, S.A. ("the '890 Publication") discloses a microwave therapy probe for treatment of the prostate. The probe includes means for cooling the urethral wall of the prostate during treatment. The probe disclosed in this publication also includes temperature measuring sensors. More specifically, the probe includes a fibre-optic temperature sensor to measure the temperature at the surface of the urethral probe, and an interstitial probe to measure the temperature inside of the prostate. The '890 Publication suggests controlling the power delivered to the probe by a microwave generator according to the temperature measured by the temperature sensors, and according to the temperature of the coolant. No further explanation as to temperature control is given in this publication. There is nothing in this publication suggesting to the person of ordinary skill in the art that the temperature of the coolant could vary.

The transurethral microwave apparatus sold by Technomed Medical Systems under the trademark PROSTATRON uses a rectal probe for monitoring treatment and an urethral probe containing the microwave antenna. Four temperature sensors are present in the apparatus: one sensor is located in the urethral probe and the other three sensors are located on the surface of a specially designed rectal probe, which sensors face the prostate. A description of this probe is given in FR-A-2 660 561.The urethral probe utilizes a coolant to cool the surface of the probe facing the urethral wall. In this apparatus, the microwave power and the temperature of the coolant are computer controlled. The coolant is kept at a constant temperature of about 20° C. Microwave power gradually increases up to about 60 W or 70 W during the first 20 minutes of the treatment. The power is then held constant unless a preset maximum temperature is measured by one of the sensors. In that case, the microwave emission is stopped to permit cooling of the rectum or the urethra and thereby prevent overheating. This technique prevents overheating the rectum wall or burning of the urethra. When the temperatures drop to below a threshold, microwave emission is resumed. This apparatus permits a shorter treatment duration, typically one session of less than one hour, and provides proper and efficient treatment of the patient.

U.S. Pat. No. 5,509,929 assigned to Technomed Medical Systems, S.A. discloses a microwave urethral probe with an inflatable balloon for anchoring the probe in the bladder of a patient. The primary active heating part of the microwave antenna is arranged to direct microwave energy on the prostatic tissues located near the bladder neck when the probe is in an operational position.

U.S. Pat. No. 5,843,144 assigned to Urologix Inc. discloses a method for treating benign prostatic hyperplasia with microwave thermal therapy. The probe described in this patent has a microwave antenna, an inflatable balloon for anchoring the probe in the bladder of the patient, and coolant duct for cooling the urethral wall near the prostate. The main heating part of the antenna is located below the bladder neck, substantially in the center of the prostate. This patent suggests minimizing the number of interruptions of microwave power applied to prostatic tissues. To achieve this result, the patent suggests applying prechilling to the urethral wall before beginning microwave treatment. The coolant is then maintained at a constant temperature during the treatment phase. After the end of the treatment, the coolant is maintained at a low temperature to reduce edema. The total duration of the treatment according to this patent is around 88 minutes, 67 minutes of which correspond to the microwave generating phases, i.e., microwave power ramping up for about 17 minutes and continuous heating of tissues for about 50 minutes. To control microwave power during the continuous heating of tissues, this patent suggests monitoring the rectal temperature and the probe temperature, and increasing or decreasing power to maintain the temperature of the rectum below 42° C. and maintain the probe temperature within 1° C. of 40° C. There is no provision for automatically adjusting the power to meet these temperature targets.

SUMMARY OF THE INVENTION

The present invention is based on the recognition that power interruptions have a negative impact on the intraprostatic temperature, and that a more efficient treatment may be achieved if such interruptions are minimized. The method of the present invention therefore provides a solution for treating tissues with a minimum number of interruptions in the delivery of microwave power. In view of the limited number of temperature measurements, the method of the present invention may easily be carried out.

The present invention also provides a solution to the problem of a shorter treatment duration. The method of the present invention thereby allows for shorter treatment duration, and thus improves patient's comfort during and after treatment.

The present invention thereby provides an apparatus for treating the prostate, having a urethral probe with a microwave antenna and ducts for circulating a coolant, a microwave generator applying microwave energy to the microwave antenna, and coolant circulating system to circulate the coolant and control the temperature of the coolant. The temperature of the coolant is controlled according to the microwave power applied to the antenna.

Preferably, the temperature of the coolant decreases as the microwave power increases. In one embodiment of the present invention, the temperature of the coolant decreases linearly as the microwave power increases. In another embodiment, the temperature of the coolant varies between a maximum value near to the temperature of the body and a minimum value lower than the temperature of the body.

The apparatus preferably includes a rectal temperature sensor. The microwave power applied to the microwave antenna is controlled according to the temperature measured by the sensor. In another embodiment, the apparatus comprises a rectal temperature sensor, and the microwave power applied to the microwave antenna is controlled only according to the temperature measured by the rectal sensor.

The apparatus may also include a feedback control to control the microwave power applied to the antenna. The feedback control may be a proportional integral feedback control. The microwave power applied to the antenna may be controlled according to the following formula:

$$\text{Power} = K \cdot \left[ (T_{Set} - T_{Measured}) + \frac{1}{\tau_i} \int (T_{Set} - T_{Measured}) \cdot dt \right]$$

with Power the power applied, $T_{measured}$ the temperature sensed by the sensor and $T_{set}$ a target temperature. In this formula, K is preferably between 5 and 20 W/°K and $\tau_i$ is preferably between 15 s and 300 s.

BRIEF DESCRIPTION OF THE DRAWINGS

A microwave therapy apparatus embodying the invention will now be described, by way of non-limiting example, and in reference to the accompanying drawing, where.

DESCRIPTION OF THE PREFERRED EMBODIMENTS

To achieve shorter treatment duration and minimize patient discomfort, the present invention includes the step of controlling the coolant temperature according to the level of microwave power. This technique allows higher levels of power to be used, while preserving the tissues surrounding the treated area. In addition, the control of the coolant temperature minimizes patient discomfort.

In one embodiment, the present invention includes the step of controlling microwave power according to rectal temperature only. This technique makes the process simpler and safer than prior art processes.

Figure 1:
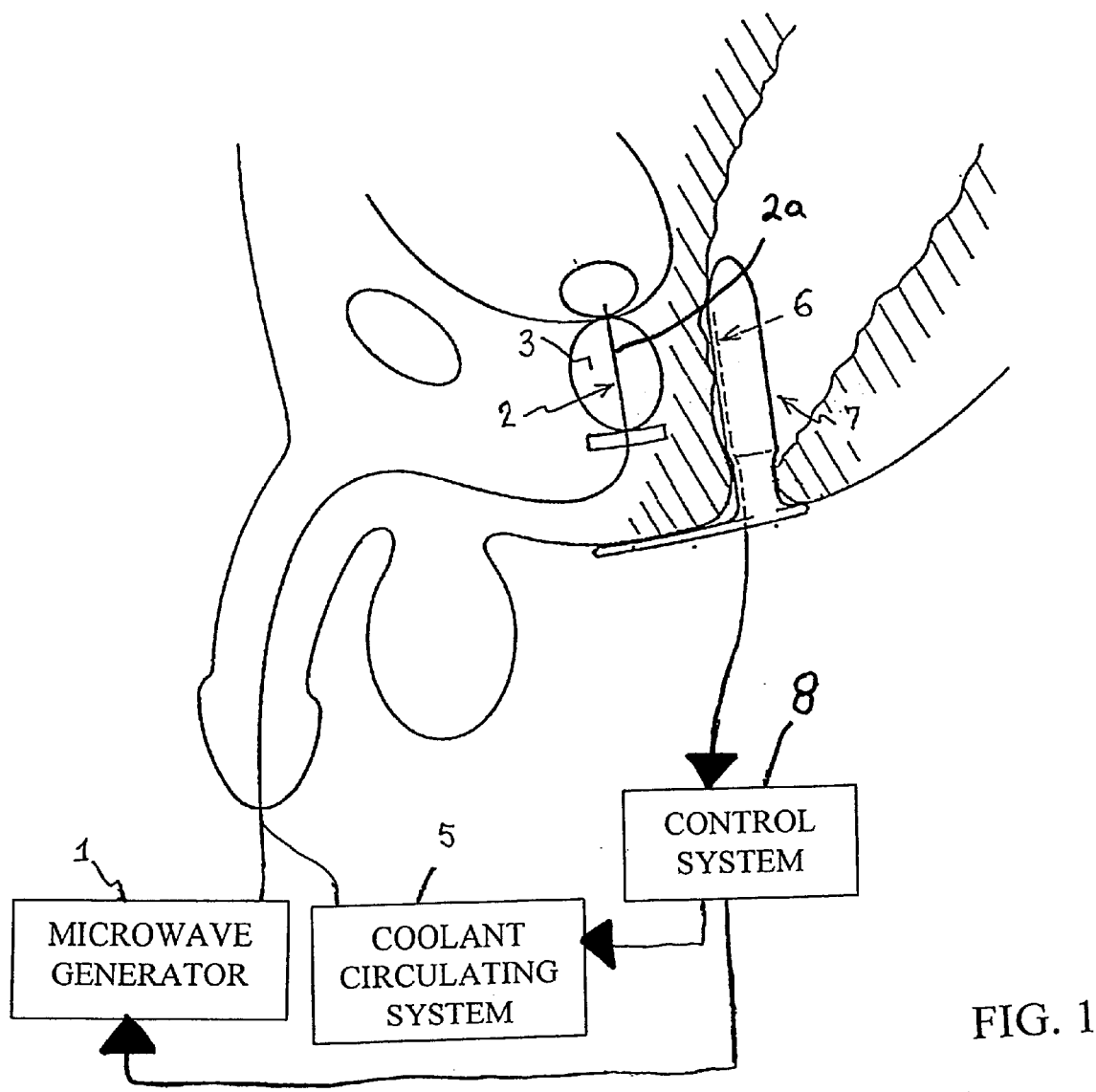
FIG. 1 is a schematic view of an apparatus for embodying the process of the present invention.

A preferred embodiment of the invention is now described. FIG. 1 shows a schematic view of an apparatus for carrying out the invention. The apparatus comprises a microwave generator 1, a urethral probe 2 having an antenna 2a that receives the microwave energy generated by the generator 1. The antenna radiates the microwave energy into tissues 3 surrounding the antenna of the probe. The probe has ducts for circulating a coolant so as to cool at least the wall of the probe near or in contact with the urethral wall. The probe may have the structure described in EP-A-0 370 890, or preferably described in U.S. Pat. No. 5,509,929 ("the '929 Patent"). As discussed above, the probe of the '929 Patent has an antenna with a main radiating point located near an anchoring balloon so that in operation, the main radiating point is located near the bladder neck.

The apparatus also includes a coolant circulating system 5 for circulating the coolant in the probe. The coolant circulating system 5 is also adapted to control the temperature of the coolant in a range from about 5 to 37° C. The coolant may be water, and the coolant circulating system may include a pump and a refrigerating device.

The apparatus also preferably includes a rectal probe 7 for monitoring rectal temperature of the patient. The probe may be of the type disclosed in EP-A-0 370 890, FR-A-2 660 561 or FR 97 09906. The probe 7 may contain a number of temperature sensors 6 that are preferably located on the side of the probe facing the prostate when the probe is inserted into the patient for operation. A person of ordinary skill in the art will appreciate that rectal temperature may be measured using means other than a rectal probe. The rectal probe 7, however, has the advantage of ensuring proper positioning of the temperature sensors so that the temperature sensors face the prostate and the urethral probe.

Last, the apparatus comprises control system 8 that receives the temperature information provided by the sensors 6 of the rectal probe 7. The control system 8 controls the microwave power provided to the probe antenna 2a by the microwave generator 1, as well as the temperature of the coolant. The interconnection of the components is illustrated in FIG. 1 by the arrows between the control system 8, the microwave generator 1 and the coolant circulating system 5, respectively.

Figure 2:
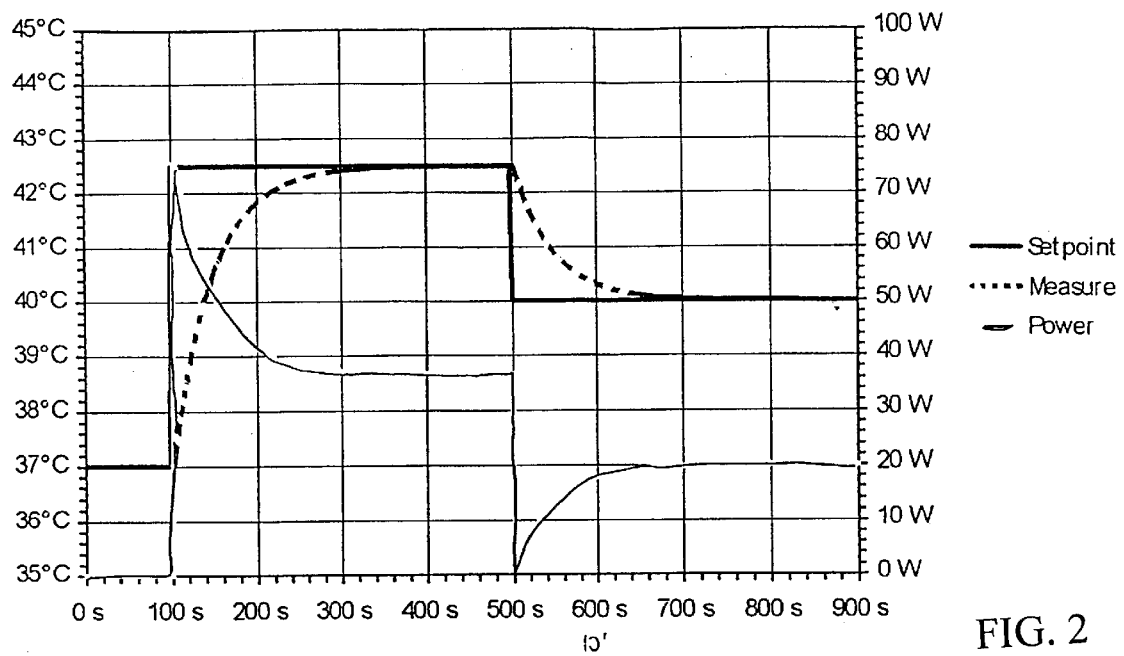
FIG. 2 is a graph of temperature and power in the apparatus of FIG. 1.

FIG. 2 is a graph of temperature and power in the apparatus of FIG. 1, illustrating the way microwave power may be controlled according to a preferred embodiment of the invention. In this embodiment, microwave power is controlled according to the temperature sensed by the temperature sensor so as to minimize the number of interruptions of microwave power. The invention proposes using a feedback control, and more specifically a proportional integral derivative ("PID") feedback control. Preferably the derivative coefficient is null.

In an other embodiment, the PID parameters are automatically adjusted as a function of temperature response of the heated tissues to a microwave impulse, thus taking into account the transfer function of the tissues. For example, in the beginning of the treatment, a microwave impulse of, for example, 80 W is delivered to the prostate and the corresponding temperature versus time profile is recorded by a recording instrument. Using this process, the PID parameters are calculated. The same procedure may be repeated several times over the duration of the treatment so that the system accounts for variations of blood perfusion caused by the heating of the tissue.

In a preferred embodiment, power is controlled according to the rectal temperature only. As compared to the power regulation proposed in U.S. Pat. No. 5,843,144, the present invention provides a simpler solution based on the premise that the temperature sensed at the urethral probe is subject to substantial variation. It is therefore preferable that this temperature is not used to set the level of microwave power.

Where the rectal probe comprises a plurality of temperature sensors, the highest temperature sensed may be used for controlling microwave power. This is notably the case for the rectal probe used in Applicant's PROSTATRON thermotherapy apparatus. Let $T_{measured}$ be the highest temperature sensed by the rectal probe sensor, and let $T_{set}$ be the target temperature. Then, the proportional integral feedback control is as follows:

$$\text{Power} = K \cdot \left( (T_{Set} - T_{Measured}) + \frac{1}{\tau_i} \int (T_{Set} - T_{Measured}) \cdot dt \right) \quad \text{Eq. (1)}$$

with Power being the power applied by the microwave generator to the urethral probe antenna, under control of the control device 8. K is a parameter representative of the power to be applied, and $\tau_i$ is a time constant representing the duration of integration in the formula given in Eq. (1). This parameter is actually representative of the weight of the integrated factor in the proportional integrated loop control. Possible values of the parameters K and $\tau_i$ are discussed below.

In the apparatus, when the Power calculated by the feedback control exceeds the maximum power of the microwave generator, then the value of the power is truncated, and the maximum possible power is delivered to the probe antenna. Conversely, when the calculated Power is below the minimum power that the microwave power generator may deliver, then the microwave generator power is switched off. Minimum and maximum microwave power may be, for example, 0 W and 80 W, respectively.

FIG. 2 shows a graph representing the behavior of the feedback control loop, for an exemplary treatment. The horizontal axis shows time, in seconds, while the vertical axis shows temperature in °C. on the left-hand side and power in Watts on the right-hand side. For the example of FIG. 2, target temperature, $T_{set}$, was set to 42.5 °C. for a duration of 400 s (between 100 and 500 s), and was thereafter set to 40° C. for a duration of 400 s (between 500 and 900 s). This is only given as an example to show the variations of power for a given temperature, but is not representative of a proposed treatment protocol according to the invention.

The graph of FIG. 2 shows that the temperature measured, $T_{measured}$, by the temperature sensor rises slowly from 37° C. to 42.5° C., and thereafter decreases slowly to reach 40° C. During this time, the power applied to the antenna 20 of the urethral probe decreases slowly from a value of 75 W to a value of 38 W. When $T_{set}$ is fixed to 40° C., the power is interrupted and thereafter slowly increases again to 20 W. These values are obtained with parameters K=13 W/K and $\tau_i$=100 s.

The graph of FIG. 2 shows that with a proportional integral feedback control, the number of interruptions of the delivery of power to the probe is minimized.

The parameters K and $\tau_i$ may be chosen as follows. Diffusion of heat in tissues is represented using the Bioheat Transfer Equation defined by H. H. Pennes (PENNES, H. H., 1948, Analysis of Tissue and Arterial Blood Temperature in Resting Forearm, *Journal of Applied Physiology*, 1, 93–122). This representation is as follows in Eq. (2):

$$\rho_t c_t \frac{\partial T}{\partial t} = k_t \nabla^2 T + q_p + q_m - wc_b(T - T_b) \qquad \text{Eq. (2)}$$

where T is the temperature, t is the time, $\rho_t$ is the tissue density, $c_t$ is the tissue specific heat, $k_t$ is the thermal conductivity, $q_p$ is the power from the outside, $q_m$ is the power from the metabolism, w is the blood perfusion, $c_b$ is the blood specific heat, and $T_b$ is the blood (or basal) temperature.

Let us define two constants, a and b as Eq. (3):

$$\begin{cases} a = \dfrac{q_m}{\rho_t c_t \cdot \text{Power}} \\ b = \dfrac{wc_b}{\rho_t c_t} \end{cases} \qquad \text{Eq. (3)}$$

a represents the influence of the microwave power on the rectal temperature, and b represents the influence of the basal and blood temperature on the rectal temperature.

By disregarding heat conductivity and metabolism-induced heat, the Bioheat Transfer Equation can be rewritten as Eq. (4):

$$\frac{\partial T}{\partial t} = a \cdot \text{Power} - b \cdot (T - T_b) \qquad \text{Eq. (4)}$$

This assumption is adequate in the case of prostate treatment. Therefore, appropriate values for K and $\tau_i$ to guarantee convergence, based on the location of the two roots of the equation are given by Eq. (5):

$$\begin{cases} K = 2 \dfrac{b}{a} \\ \tau_i = \dfrac{1}{b} \end{cases} \qquad \text{Eq. (5)}$$

Reasonably good approximations for a and b are: a=0.0015 °K/W·s and b=0.010 s$^{-1}$. This leads to: K=13 W/°K and $\tau_i$=100 s.

Treatment using this embodiment of the invention proved efficient, and permitted the total duration of treatment to be reduced considerably, as discussed below.

The present invention also preferably regulates the temperature of the coolant according to the power delivered by the microwave generator. This is contrary to the teachings of U.S. Pat. No. 5,843,144, where the temperature of the coolant is kept at a constant level during treatment while the microwave power is delivered to the probe antenna under manual control. Preferably, the temperature of the coolant varies between a maximum value, which is near to the temperature of the body, to a minimum value, which is lower than the temperature of the body. The minimum value may be chosen according to the coolant and to the circulating device, and if water is used as a coolant, the minimum value may be, for example, about 5° C.

This feature of the invention permits more efficient use of microwave power. Indeed, when power is low, that is, when the temperature, $T_{measured}$, is near the target temperature, $T_{set}$, the temperature of the coolant is close to the temperature of the body. This ensures that the energy radiated by the antenna is used to heat the tissues and maintain tissue temperature at the set temperature. The fact that the coolant temperature is still lower than the temperature of the body protects the urethral wall.

On the other hand, when power is high, that is, when the temperature, $T_{measured}$, is far from the target temperature, $T_{set}$, the temperature of the coolant is low. This ensures that the urethral wall is protected, notwithstanding the high amount of energy radiated by the antenna.

Figure 3:
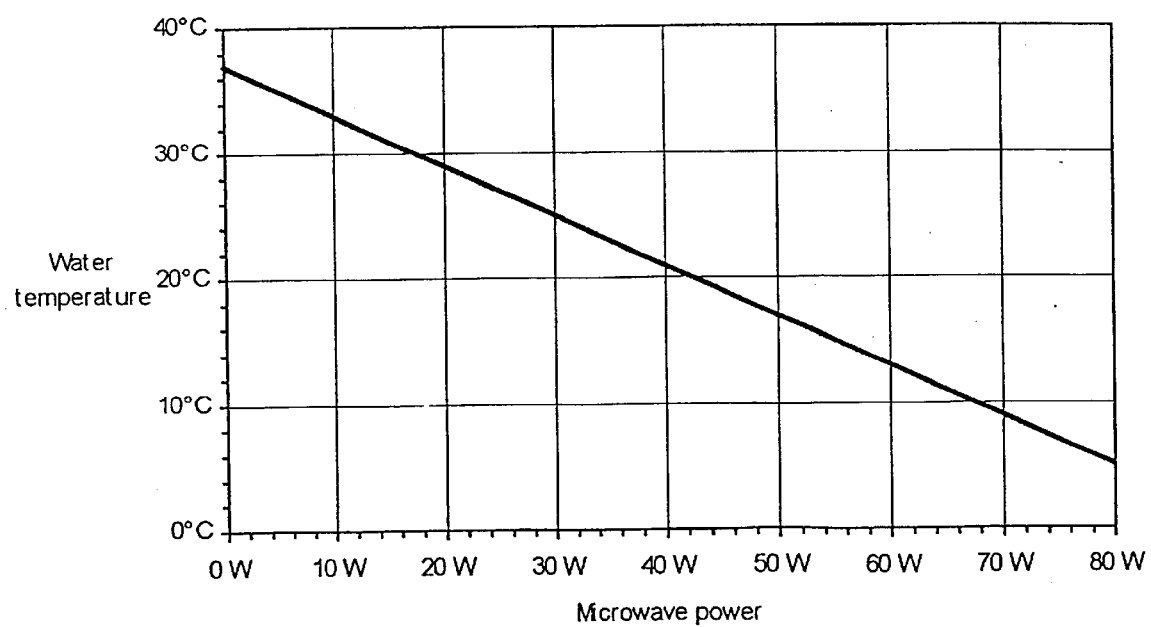
FIG. 3 is a graph of temperature of the coolant according to microwave power.

FIG. 3 shows another embodiment of the invention, where temperature of the coolant decreases linearly as a function of the radiated power. For a minimum value of the power, the temperature of the coolant is set to body temperature of 37° C. For a maximum value of the power of 80 W in the exemplified graph, the temperature of the coolant is set to 5° C., which is the minimum temperature achievable by the circulating device.

The method of the present invention thereby maximizes heat applied to the prostate, while minimizing patient discomfort and protecting the urethral wall.

Clinical studies were carried out using the urethral probe disclosed in U.S. Pat. No. 5,509,929, using a proportional integral feedback power regulation and a coolant temperature regulation according to the invention. $T_{set}$ was fixed to 42.5° C. for a period of 30 minutes. Treatment proved as efficient as the treatment using the usual PROSTATRON thermotherapy apparatus. The patient did not suffer any discomfort, and the total duration of treatment was about 30 minutes, rather than one hour.

To summarize, the process for treating the prostate tissues includes (1) inserting a urethral probe within the urethra of a patient to position a microwave antenna adjacent to the prostate, the probe being cooled by a coolant; (2) applying microwave energy to the antenna; and (3) controlling the temperature of the coolant according to the microwave power applied to the antenna.

As discussed above, the temperature of the coolant decreases when the power applied to the antenna increases. The temperature of the coolant preferably decreases linearly with the power applied to the antenna. The temperature of the coolant is preferably at the lowest value when the power is at the highest level. It is preferable that the temperature of the coolant is near the temperature of the body when the microwave power is a minimum value.

The process may also include inserting a temperature sensor into the rectum of a patient. In this case, the microwave energy applied to the antenna may be controlled according to the temperature sensed by the rectal temperature sensor. The microwave energy applied to the antenna may be controlled according to the sensed rectal temperature only, which is contrary to the prior art. Of course, this means that other sensed temperatures are not taken into account, but other parameters, such as time, may be taken into account. For this purpose, a proportional integral feedback loop may be used.

The invention is not limited to the embodiments disclosed in the description. For example, one may use not only a proportional integral feedback control, but other types of feedback controls, which allows progressive variations of microwave power for adapting the power delivered. One embodiment of the invention discloses that power was controlled according to the temperature sensed by temperature sensor, and where the temperature of the coolant was controlled according to the power. However, it is possible to control of the temperature of the coolant according to the temperature sensed by the temperature sensors In one embodiment of the invention, temperature of the coolant was controlled according to the microwave power applied to the urethral probe by the generator. One could also carry out the invention by measuring the level of microwave power in the tissues of the patient, or in the rectum of the patient. In the preferred embodiment, the control element is separate from the microwave generator and from the coolant circulating means. The control means may also be integrated with the coolant circulating means, or with the microwave generator.

The invention was described in reference to treatment of benign prostate hyperplasia. It is also possible to use the concepts of the present invention with other types of prostate diseases.

What is claimed is:

1. An apparatus for treating the prostate, the apparatus comprising:
   a urethral probe with a microwave antenna and ducts for circulating a coolant;
   a rectal temperature sensor;
   a microwave generator applying microwave energy to the microwave antenna that is controlled only according to the temperature measured by the rectal temperature sensor; and
   a coolant circulating system to circulate the coolant and control the temperature of the coolant, wherein the temperature of the coolant is controlled according to the microwave energy applied to the antenna.

2. The apparatus of claim 1, wherein the temperature of the coolant decreases as the microwave energy increases.

3. The apparatus of claim 2, wherein the temperature of the coolant decreases linearly as the microwave energy increases.

4. The apparatus of claim 3, wherein the temperature of the coolant varies between a maximum value near to the temperature of the body and a minimum value lower than the temperature of the body.

5. An apparatus for treating the prostate, the apparatus comprising:
   a urethral probe with a microwave antenna and ducts for circulating a coolant;
   a sensor for measuring a temperature of tissue;
   a microwave generator applying microwave energy to the microwave antenna, the microwave energy applied to the antenna being controlled according to the following formula:

$$\text{Power} = K \cdot \left[ (T_{Set} - T_{Measured}) + \frac{1}{\tau_i} \int (T_{Set} - T_{Measured}) dt \right]$$

where Power is the power applied, $T_{measured}$ is the temperature measured by the sensor and $T_{set}$ is a target temperature; and a coolant circulating system to circulate the coolant and control the temperature of the coolant, wherein the temperature of the coolant is controlled according to the microwave energy applied to the antenna.

6. The apparatus of claim 5, wherein K is between 5 and 20 W/°K.

7. The apparatus of claim 5, wherein $\tau_i$ is between 15 s and 300 s.

8. A method for treating the prostate, the method comprising the steps of:
   inserting a urethral probe into a urethra;
   providing microwave energy to a microwave antenna in the urethral probe;
   measuring temperature with a rectal temperature sensor;
   adjusting the microwave enertty applied to the microwave antenna according only to the temperature measured by the rectal temperature sensor; and
   circulating a coolant through the urethral probe, wherein a temperature of the coolant is controlled according to the microwave energy applied to the antenna.

9. The method of claim 8, wherein the temperature of the coolant decreases as the microwave energy increases.

10. The method of claim 9, wherein the temperature of the coolant decreases linearly as the microwave energy increases.

11. The method of claim 10, wherein the temperature of the coolant varies between a maximum value near to the temperature of the body and a minimum value lower than the temperature of the body.

12. A method for treating the prostate, the method comprising the steps of:
   inserting a urethral probe into a urethra;
   measuring a temperature of tissue;
   providing microwave energy to a microwave antenna in the urethral probe, the microwave energy applied to the antenna being controlled according to the following formula:

$$\text{Power} = K \cdot \left[ (T_{Set} - T_{Measured}) + \frac{1}{\tau_i} \int (T_{Set} - T_{Measured}) dt \right]$$

where Power is the power applied, $T_{measured}$ is the temperature measured by the sensor and $T_{set}$ is a target temperature; and circulating a coolant through the urethral probe, wherein a temperature of the coolant is controlled according to the microwave energy applied to the antenna.

13. The method of claim 12, wherein K is between 5 and 20 W/°K.

14. The method of claim 12, wherein $\tau_i$ is between 15 s and 300 s.

15. A method for treating the prostate, the method comprising the steps of:
   inserting a urethral probe into a urethra;
   providing a testing profile of microwave energy to a microwave antenna in the urethral probe;
   recording a response characteristic of tissue from the testing profile of microwave energy provided to the microwave antenna;

calculating control parameters based on the recorded response characteristic;

providing microwave energy to the microwave antenna in the urethral probe;

measuring tissue temperature;

adjusting the microwave energy applied to the microwave antenna with a feedback control based on the measured tissue temperature and using the calculated control parameters; and circulating a coolant through the urethral probe, wherein a temperature of the coolant is controlled according to the microwave energy applied to the antenna.

16. The method of claim 15, further comprising repeating the steps of providing testing profile of microwave energy, recording a response characteristic of tissue and calculating control parameters during the treating of the prostate.

17. The method of claim 15, wherein the feedback control is a proportional integral feedback and the control parameters are coefficients of the proportional and integral terms of the feedback control.

18. A method for treating the prostate, the method comprising the steps of:

inserting a urethral probe into a urethra;

providing a testing profile of microwave energy to a microwave antenna in the urethral probe;

recording a response characteristic of tissue from the testing profile of microwave energy provided to the microwave antenna;

calculating at least one of proportional, integral and derivative control parameters of a proportional-integral-derivative (PID) feedback control system based on the recorded response characteristic;

providing microwave energy to the microwave antenna in the urethral probe;

measuring tissue temperature;

adjusting the microwave energy applied to the microwave antenna with the PID feedback control system based on the measured tissue temperature and using the calculated proportional, integral and derivative control parameters; and circulating a coolant through the urethral probe, wherein a temperature of the coolant is controlled according to the microwave energy applied to the antenna.

19. The method of claim 18, further comprising repeating the steps ot providing testing profile of microwave energy, recording a response characteristic of tissue and calculating at least one of proportional, integral and derivative control parameters during the treating of the prostate.

20. A method for treating the prostate, the method comprising the steps of:

inserting a urethral probe into a urethra;

providing microwave energy to a microwave antenna in the urethral probe in a unit step profile with a predetermined peak magnitude;

measuring tissue temperature;

adjusting the microwave energy applied to the microwave antenna with a feedback control based on the measured tissue temperature; and circulating a coolant through the urethral probe, wherein a temperature of the coolant is controlled according to the microwave energy applied to the antenna.

* * * * *

UNITED STATES PATENT AND TRADEMARK OFFICE
CERTIFICATE OF CORRECTION

PATENT NO.    : 6,272,384 B1
DATED         : August 7, 2001
INVENTOR(S)   : Eric Simon et al.

Page 1 of 1

It is certified that error appears in the above-identified patent and that said Letters Patent is hereby corrected as shown below:

Column 8,
Line 22, delete "enertty", insert -- energy --

Column 10,
Line 14, delete "ot", insert -- or --.

Signed and Sealed this

Seventh Day of May, 2002

*Attest:*

*Attesting Officer*

JAMES E. ROGAN
*Director of the United States Patent and Trademark Office*